(12) United States Patent
Leitner et al.

(10) Patent No.: US 10,894,013 B2
(45) Date of Patent: *Jan. 19, 2021

(54) COMPOSITION AND METHOD FOR REDUCING ALLERGIC RESPONSE

(71) Applicant: PROLLERGY CORPORATION, Sherman Oaks, CA (US)

(72) Inventors: Andrew Leitner, Encino, CA (US);
Katie Marks, Los Angeles, CA (US);
Aaron Rowe, Toluca Lake, CA (US);
Daniel Zakowski, Sherman Oaks, CA (US)

(73) Assignee: PROLLERGY CORPORATION, Sherman Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/709,321

(22) Filed: Dec. 10, 2019

(65) Prior Publication Data

US 2020/0113822 A1 Apr. 16, 2020

Related U.S. Application Data

(63) Continuation of application No. 16/197,919, filed on Nov. 21, 2018.

(60) Provisional application No. 62/595,290, filed on Dec. 6, 2017.

(51) Int. Cl.

| | | |
|---|---|---|
| *A61K 39/35* | (2006.01) |
| *A61K 39/00* | (2006.01) |
| *A61K 9/00* | (2006.01) |
| *A61K 9/16* | (2006.01) |
| *A23L 33/185* | (2016.01) |
| *A23L 33/00* | (2016.01) |
| *A23L 33/19* | (2016.01) |

(52) U.S. Cl.
CPC .......... *A61K 9/0053* (2013.01); *A23L 33/185* (2016.08); *A23L 33/19* (2016.08); *A23L 33/40* (2016.08); *A61K 9/16* (2013.01); *A61K 39/35* (2013.01); *A23V 2002/00* (2013.01); *A61K 9/0056* (2013.01); *A61K 2039/54* (2013.01); *A61K 2039/545* (2013.01); *A61K 2039/55* (2013.01); *A61K 2039/577* (2013.01)

(58) Field of Classification Search
None
See application file for complete search history.

(56) References Cited

U.S. PATENT DOCUMENTS

| | | | | |
|---|---|---|---|---|
| 9,724,271 B2 * | 8/2017 | Francois | ............... | A61J 7/0053 |
| 2013/0218132 A1 * | 8/2013 | Francois | ............... | A61J 7/0053 |
| | | | | 604/514 |
| 2016/0263212 A1 * | 9/2016 | Friedman | ............... | A61K 31/07 |
| 2017/0360922 A1 * | 12/2017 | Turke | ................. | A61K 39/35 |

* cited by examiner

*Primary Examiner* — Nora M Rooney
(74) *Attorney, Agent, or Firm* — Karish & Bjorgum, PC

(57) ABSTRACT

A method and kit for the sequential early introduction to an infant of at least two allergens to decrease the infant's risk for developing allergies, the method involving administering an initial lower, exposure dose of a first allergen for a day or two, followed by administering a higher maintenance dose of the first allergen for several days, followed by administering the maintenance dose of the first allergen and an initial lower, exposure dose of a second allergen for a day or two, followed by administering the higher maintenance dose of the first allergen and a higher maintenance does of the second allergen for several days. The allergens can be provided in powdered protein form in premeasured pouches for addition to baby formula or to mother's milk. Alternatively, the allergens can already be provided in baby formula, or in other foods such as snack bars, cookies, or gels.

19 Claims, 3 Drawing Sheets

|  | Dose (in grams of protein) | | | |
|---|---|---|---|---|
|  | DAY | COW'S MILK | EGG WHITE | PEANUT |
| EXPOSURE PHASE | 1 | 0.2 | | |
|  | 2 | 0.2 | | |
|  | 3 | 0.57 | | |
|  | 4 | 0.57 | | |
|  | 5 | 0.57 | 0.025 | |
|  | 6 | 0.57 | 0.025 | |
|  | 7 | 0.57 | 0.125 | |
|  | 8 | 0.57 | 0.125 | |
|  | 9 | 0.57 | 0.125 | 0.1 |
|  | 10 | 0.57 | 0.125 | 0.1 |
|  | 11 | 0.57 | 0.125 | 0.43 |
|  | 12 | 0.57 | 0.125 | 0.43 |
| MAINTENANCE PHASE | 13 - | 0.57 | 0.125 | 0.43 |

Figure 1
Three Allergen Early Introduction System Kit Dosing

|  |  | Dose (in grams of protein) | | | | |
| --- | --- | --- | --- | --- | --- | --- |
|  | DAY | COW'S MILK | EGG WHITE | PEANUT | WHEAT | SOY |
| EXPOSURE PHASE | 1 | 0.2 |  |  |  |  |
|  | 2 | 0.2 |  |  |  |  |
|  | 3 | 0.57 |  |  |  |  |
|  | 4 | 0.57 |  |  |  |  |
|  | 5 | 0.57 | 0.025 |  |  |  |
|  | 6 | 0.57 | 0.025 |  |  |  |
|  | 7 | 0.57 | 0.125 |  |  |  |
|  | 8 | 0.57 | 0.125 |  |  |  |
|  | 9 | 0.57 | 0.125 | 0.1 |  |  |
|  | 10 | 0.57 | 0.125 | 0.1 |  |  |
|  | 11 | 0.57 | 0.125 | 0.43 |  |  |
|  | 12 | 0.57 | 0.125 | 0.43 |  |  |
|  | 13 | 0.57 | 0.125 | 0.43 | 0.1 |  |
|  | 14 | 0.57 | 0.125 | 0.43 | 0.1 |  |
|  | 15 | 0.57 | 0.125 | 0.43 | 0.43 |  |
|  | 16 | 0.57 | 0.125 | 0.43 | 0.43 |  |
|  | 17 | 0.57 | 0.125 | 0.43 | 0.43 | 0.1 |
|  | 18 | 0.57 | 0.125 | 0.43 | 0.43 | 0.1 |
|  | 19 | 0.57 | 0.125 | 0.43 | 0.43 | 0.43 |
|  | 20 | 0.57 | 0.125 | 0.43 | 0.43 | 0.43 |
| MAINTENANCE PHASE | 21 - | 0.57 | 0.125 | 0.43 | 0.43 | 0.43 |

Figure 2
Five Allergen Early Introduction System Kit Dosing

Exemplary Stick Packs with Allergen Powder

COMPOSITION AND METHOD FOR REDUCING ALLERGIC RESPONSE

CROSS-REFERENCE TO RELATED APPLICATION

This application is a Continuation application that claims priority of U.S. Ser. No. 16/197,919 filed on Nov. 21, 2018 which also claims priority from U.S. Provisional Patent Application No. 62/595,290, entitled "COMPOSITION AND METHOD FOR REDUCING ALLERGIC RESPONSE", and filed Dec. 6, 2017.

FIELD OF THE INVENTION

The invention relates to allergies, and more particular an enteral composition and method for the sequential early introduction of allergens to decrease a user's risk for developing food and other allergies.

BACKGROUND OF THE INVENTION

Food allergies have become increasingly prevalent over the past two decades, particularly in developed nations. One in thirteen children in developed nations have a food allergy, and all food allergies are caused by exposure to food proteins. Population studies from several countries have demonstrated this trend, including a rise in pediatric hospitalizations and anaphylaxis. Much work has been done to understand the underlying mechanisms of food allergy and reasons for its increasing prevalence. Environmental factors and epigenetics have been implicated as likely contributors. For instance, studies have shown that migrants appear to acquire the incident risk of their adopted country, suggesting genetics alone cannot explain the trend.

In recent times, infants are not being exposed to food the way they have been through most of human history. There is significant anthropologic evidence supporting the practice of early introduction of foods to breastfed infants. Diet diversity has been a component of infant feeding for most of human civilization for thousands of years, including through masticated foods given to infants for supplementation. It is likely that the movement away from these practices and other complementary feeding customs is correlated with increased food allergy incidence.

Recent randomized controlled trials on early introduction of highly allergenic foods have shown a correlated reduction in food allergy incidence. In 2015, the Learning Early About Peanut Allergy (LEAP) trial demonstrated a greater than 80% reduction in peanut allergy rates in those infants exposed regularly to peanut protein compared to those who avoided consumption. The following year, per-protocol results from The Enquiring About Tolerance (EAT) study showed a two-thirds reduction of food allergy in those infants fed multiple food allergens regularly starting at 3-4 months of age. These studies also inform an effective quantity of allergen protein for administration to children in this age range, in terms of grams per week sustained over time.

The scientific basis for these results can be found in the "dual allergen exposure hypothesis," first described by Dr. Gideon Lack. According to this theory, exposure to allergens from cutaneous (skin) sources lends to sensitization and a higher risk of food allergy development. On the other hand, exposure via the intestine (gut) promotes tolerance and is likely protective. By encouraging an extended avoidance of allergenic foods, our previous medical dietary guidelines may have unwittingly promoted the increased rates of food allergy because of decreased levels of gut tolerance in the population.

Based on the results of these significant trials, there has been a remarkable paradigm shift in how experts view the timing of food allergen exposure to infants. This has resulted in the rapid evolution of many US and international guidelines regarding infant diet recommendations. In 2008, the American Academy of Pediatrics reversed its previous position where it had recommended avoidance of cow's milk for 12 months, egg for 24 months, and nuts and fish for 36 months in high risk infants. In 2010, the National Institute of Allergy and Infectious Diseases (NIAID) issued new guidelines recommending against the delay of food introduction beyond four to six months of age. In 2017, the NIAID further recommended early age-appropriate introduction of peanuts for all infants and especially in those at risk for development of food allergy. As recently as Sep. 7, 2017, the FDA issued its first-ever qualified health claim advising that early introduction of peanuts to certain high-risk infants may reduce the risk of peanut allergy. Other countries have issued similar guidance, including an Australian Consensus stating that "all infants should be given allergenic solid foods including peanut butter, cooked egg, dairy, and wheat products in the first year of life. This includes infants at high risk of allergy." Thus, the extent to which guidance from pediatricians and allergists regarding early introduction has shifted cannot be overstated and we are looking at a sea change in approach from just a decade ago.

Unfortunately, early introduction is difficult to accomplish, and there is still no mechanism for families to achieve easy and effective early introduction of multiple food allergens for their babies. While initial study protocols (such as LEAP and EAT) have been effective, they are very difficult to comply with. In the case of LEAP, parents were contacted 104 times over the course of the study to ensure compliance. For the EAT study, only 56% of parents were able to maintain the feeding requirements, which included fairly large amounts of solid foods in infants who had not started eating otherwise and had certain difficulties doing so. For the EAT study, this was a critical factor: the reduction in food allergy was only shown to be statistically significant in the group of families who were able to maintain a certain level of compliance. Any family can attest to the difficulty of getting young children to consistently eat one food, let alone multiple, especially at such a young age.

Furthermore, there are many children who have already developed signs of food allergy on testing by the age of six months. This is telling us that even with these newer efforts, we are not starting early enough. In the LEAP study, 9% of children with allergy risk factors were excluded at enrollment because they already tested positive for peanut allergy on skin prick testing. As described further below, the inventors have discovered that very early introduction of allergenic proteins, perhaps to newborn or infants within the first weeks of life, may be an appropriate time to start the introduction.

A population level intervention is needed for significant improvement in the food allergy epidemic. Traditionally defined "high risk" children only represent a minority of the total food allergy population. Even with rigorous early introduction studies, some enrolled infants already demonstrated positive food challenges, suggesting earlier ages of exposure would be merited. Moreover, currently utilized food allergy testing has significant limitations. It is not necessary and certainly not feasible for every infant to see an allergist before starting to eat. In fact, there are significant downsides of excessive screening tests for food allergy, such as skin prick tests, which can trigger recommendations to avoid certain foods which otherwise would not produce clinical symptoms of food allergy.

These issues are compounded because it appears that there is a relatively narrow immunological developmental window during which infants can acquire their ability to handle allergens without having allergic reactions. If this immunological developmental window is missed, e.g., because of avoidance of allergens, it may be too late.

While it would be desirable to ameliorate this problem by introducing solid foods at an early age, this can be a challenge because many infants are not yet developmentally ready for solid food, and it can be difficult for busy parents with young infants to stick to a regimen.

Accordingly, there remains a need for compositions and methodology for introducing multiple food allergens (at specified dose amounts of protein) to infants younger than 6 months of age that also simplifies and helps standardize early exposure and limit the need for universal screening or other unrealistic and unreliable public health measures.

SUMMARY OF THE INVENTION

The present invention is a multiple allergen early introduction system, in the form of a kit which includes an outer container (box, bag, pouch, tin) containing individually packaged single use portions, preferentially in a stick pack with protein powders and other substances. The protein powders are formulated to readily suspend in breastmilk or infant formula and are of a particle size that readily passes through the nipple of common infant bottles. These components achieve their purpose through adherence to the daily and guided system of early introduction. During the exposure phase, food proteins representing major food allergens are introduced one by one and with graded dose increases with a stepwise daily packet. Additional food allergens are added over the course of multiple days. During the maintenance phase, sustained amounts of all of the relevant food allergens are administered through ongoing daily packets. These are continued daily until routine diet diversity is achieved from the regular consumption of solid foods.

In lieu of providing the multiple allergen early introduction system in the form of a kit which includes an outer container (box, bag, pouch, tin) with individually packaged single use portions, which are to be added by the users to infant formula or mother's milk, the multiple allergens can be provided as already mixed in with infant formula. For example, infant formula could be provided in a staged kit, with the infant formula progressing through different formulations that introduce and then bring up the level of the various allergens until a final, maintenance infant formula is reached, and then that maintenance infant formula can continue to be given to the infant for a time. In addition to a staged kit, an infant formula containing a maintenance level of the multiple allergens at their maintenance doses can be provided. The advantage of such a maintenance level of such a formulation would be that once the maintenance level of the allergens is reached, this would obviate the need for consumers to add the single use portions of multiple allergens each time a bottle of infant formula is prepared.

Another embodiment of the invention can include providing a kit of the allergens as noted above, but instead of providing the allergens in pre-measured dry powders to be added to infant formula or mother's milk, they can be provided as individually packaged single use gels portions which can be administered into the infant's mouth during feedings.

A further embodiment of the invention can include providing the multiple allergens in pre-prepared foods, such as providing the multiple allergens in baby food in jars, pouches, packs, etc., or in the form of snack bars, "cookies", and the like. Such forms would be especially appropriate for infants once they begin eating baby food and would be ideal for formulations at the maintenance level of allergens.

The system may also have one or more of the following: (a) Exposure packets and maintenance packets that can be introduced earlier than current national feeding guidelines of four (4) months, should these guidelines change. Indeed, the inventors have determined that some infants are already sensitized to certain allergens, e.g., peanuts, at the age of four months and therefore believe that the allergens of the invention should start to be administered to infants earlier than four months, and perhaps as early as the first days or weeks of life. Indeed, the same formulation could be used as early as the neonatal period. (b) Exposure and maintenance packets that can also be mixed in solid foods, if the infant is developmentally ready. (c) Exposure and maintenance powders pre-mixed in liquid, such as water or liquid infant formula. (d) Exposure and maintenance powders in a slurry formulation, for additional routes of administration, including via a daily dispensing pacifier. (e) Other non-protein additives to boost immune and intestinal health during early introduction. These may include but are not limited to: one or more vitamins, such as Vitamin D3, live cultures, probiotics, or prebiotics. (f) Other non-protein additives for use as a dietary supplement, including but not limited to: stabilizers, emulsifiers, anti-caking agents, sweeteners, or flavoring. (g) A supplement kit of additional food allergens for use after certain time has elapsed on the maintenance phase. These food allergens can include but are not limited to: tree nuts, whitefish, shellfish, wheat, soy, and sesame. This supplement kit would likewise be in the form of a kit which includes an outer container (box, bag, pouch, tin) containing individually packaged single use portions, preferentially in a stick pack with protein powders and other substances. (h) A supplement kit of additional non-food allergens deemed appropriate for early introduction, including but not limited to: pet and other non-food animal allergens, pollen and other seasonal allergens, or medication allergens.

These and other features of the invention are described below.

BRIEF DESCRIPTION OF THE DRAWINGS

FIG. 1 is a table showing the dosing regimen for an exemplary three-allergen early introduction kit of the invention.

FIG. 2 is a table showing the dosing regimen for an exemplary five-allergen early introduction kit of the invention.

DETAILED DESCRIPTION

Figure 3:
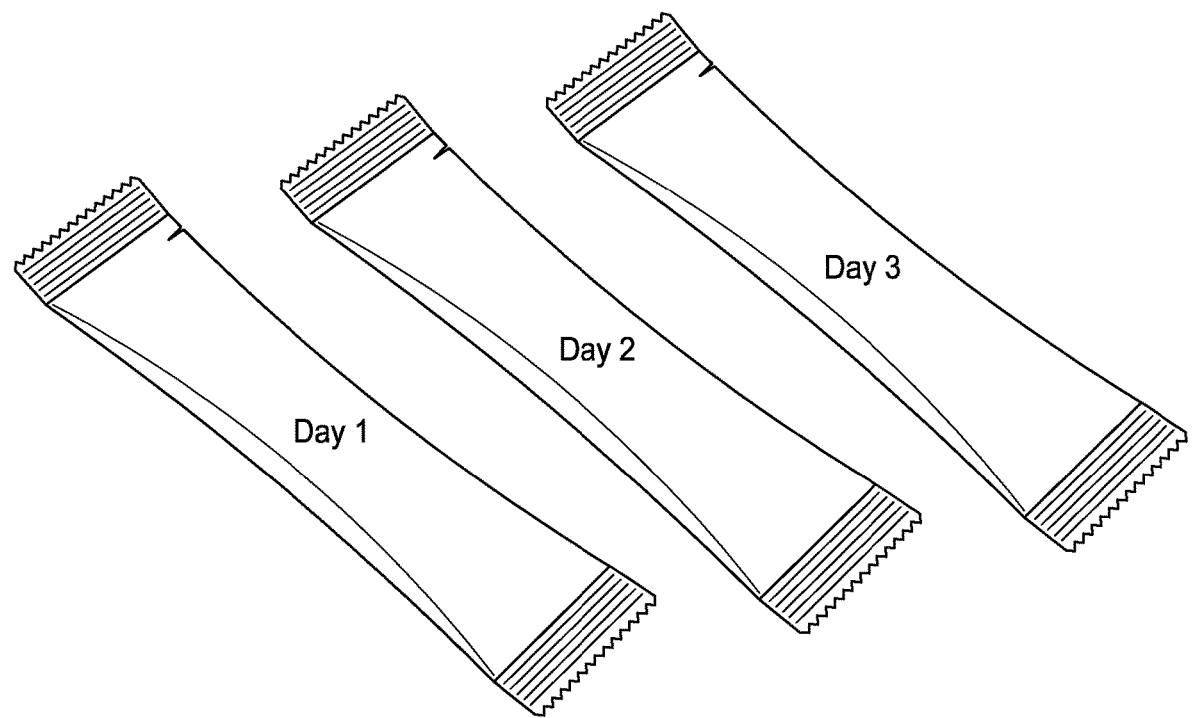
FIG. 3 is front of three stick packs marked with day number for an exemplary formulation of the kit of invention.

The invention is a ground-breaking solution to the difficulties infant caretakers face with early food introduction for infants. It is a dietary supplement aimed at broad adoption and a substantial reduction of food allergies on a population level. This supplement, a powder that mixes easily with breast milk or formula or in infant foods, includes "culprit allergens" from the foods most commonly associated with childhood food allergy. Made from the powder of natural foods, the daily dose regimen has been formulated specifically to promote the development of tolerance via the gastrointestinal system. While it is impossible to prevent all reactions to food, our dosing regimen is specifically designed to ensure that reactions are mild and identified early, if they occur. In addition to the evidence-based dose escalation noted above, another innovative feature involves sequential introduction of food allergens.

Through easy-to-follow daily use with breastmilk or formula, starting at about four months of age, infants will be exposed to common food allergens during the key critical window of immune development. In one embodiment of the invention, the maintenance formulation includes three allergens, namely cow's milk, egg, and peanut, which together represent over 80% of all childhood food allergies. It is noted that while cow's milk is used, cow's milk yogurt or whey and casein powder can be used instead. Other kits can encompass additional proteins, addressing the vast majority of all causes of IgE-mediated food allergy. The dosing regimen is evidence-based, drawn from the methodology of recent randomized trials as well as published clinical experience with oral food challenges in allergists' offices. Parents and other caregivers can take comfort in a dosing regimen developed by allergists, specifically designed to reduce the risk of food allergy development and with safety as the constant priority.

What the invention is not, is the introduction of microdoses or homeopathic approaches. There is a widely-described concern among allergists that introducing allergens at doses that are 1) too low and 2) too infrequent can in fact promote the sensitization pathway and therefore increase rather than reduce food allergy incidence. Through the innovative, gentle and gradual daily dosing regimen, the inventors have maximized the efficacy of the method and kit while adhering to strict safety considerations.

In a preferred embodiment, the multiple allergen early introduction system is a kit comprising daily dietary supplements and instructions for use. The system is a stepwise program of daily use, administered to infants via suspension of the supplement powder in breast milk, formula, or solid foods. The daily program incorporates increases in protein exposure, sequential introduction, and promotion of tolerance. First exposure formulations use protein amounts determined to be in a range of low provoking doses, as established in the medical literature. By utilizing low provoking doses, reactions if they do occur are significantly more likely to be mild in nature. In the event of any reaction, including but not limited to rashes or gastrointestinal upset, parents and other caregivers are able to present an exact description of exposure history to their pediatrician or allergist. This approach is truly ground-breaking in its ability to reduce the burden of confusing and inconsistent testing that children face when they experience any food reactions in current practice. Focused testing is proven to be the best approach to allergy diagnosis, and our dosing regimen allows families to do just that.

After it has been confirmed that the exposure dose of a particular protein is well tolerated, the infant will continue to be given packets of protein, which subsequent packets will include a higher, "maintenance" dose of the now cleared protein. Thus, each day's supplement involves either 1) duplication of previous allergen amounts to promote tolerance and allow for detection of delayed reactions, 2) increase of previous allergen amount to achieve maintenance dosing levels, or 3) addition of a new food allergen for sequential introduction. Once an allergen has been introduced, it is included in all subsequent days of the guided program.

The "exposure" phase involves graded increases in allergen amount as well as sequential introduction of new allergens. Once maintenance levels of each have been attained, continuation at these levels is done through daily administration during the "maintenance" phase.

An exemplary introduction kit contains a 30-day supply consisting of daily supplements for both the exposure and maintenance phase. Busy mothers, whether breastfeeding, pumping, formula feeding, or some combination of these three, will benefit from the ease of use of the kit and method. Moreover, absolutely no changes in feeding practices are needed for this program. The product's powder comes in easily portable packets and no extra supplies are needed.

Continuation kits contain the maintenance phase formulations only. The formulations and duration of the exposure phase depends on the number and type of allergens introduced. FIG. 1 is an exemplary dosing chart for a three-allergen introduction system. FIG. 1 is illustrative, but the guided system is not limited to a three-allergen system and the method described above applies to additional allergens as well.

The dosing chart includes initial dosing derived from "low provoking dose" data as well as protocols from food allergy prevention studies including LEAP, EAT, and PETIT.

The food allergen proteins are sourced from the powders of whole foods. These whole food powders are verified to be pure and limited to the specific whole food as well as produced via good manufacturing practices. For the referenced exemplary three-allergen example, the protein powders consist of organic cow's milk, organic cooked egg white, and organic peanut powder.

FIG. 1 lists the representative protein components of a three-allergen early introduction system. The daily supplement can also include 400 IU of Vitamin D3, probiotics including but not limited to *Streptococcus thermophilus* and *Lactobacillus delbrueckii* ssp *bulgaricus* (both of which are used in the production of cow's milk yogurt) and *Bifidobacterium infantis*. The powders are preferably made by known techniques including freeze or spray drying, milling, sifting, vibratory sifting, and vacuum odor removal of the various products In its most complete form, the kit of the invention is made up of the following components. Daily supplements are provided in the form of a powder contained within a specifically labeled package, such as a stick pack or sealed pouch. Hereinafter the inventor refers to the packaging as a stick pack but the format can be as desired. The stick pack specifies the day within the guided system, preferably both through verbiage and pictorially, e.g., DAY 1, DAY 2, . . . . DAY 30. The stick packs themselves may preferably be arranged within a box with a designated sequence. The box contains written instructions printed on the packaging as well as an insert. Combined, these components make up the multiple allergen early introduction system kit.

The most complete form of performing the method associated with the disclosed device consists of the following steps: On a daily basis, and according to the instructions for use, the infant's caregiver is to tear open the indicated stick pack, empty its contents into either 1) an infant bottle containing breast-milk, 2) an infant bottle containing infant formula, or 3) a bowl of infant food. For options 1) and 2), the bottle is to be swirled gently until the powder is in suspension. For option 3), the content is stirred into the infant food. The bottle or infant food is then to be preferably given to the infant within five minutes. If there is a delay in administration or any settling is noticed, the bottle will again be swirled gently prior to feeding. The entire contents of each stick pack are to be consumed by the infant daily during the guided system. Empty stick packs are to be disposed.

The maintenance phase stick packs are to be continued daily until the infant is tolerating a wide range of solid foods ensuring diet diversity. Once the initial introduction kit has been completed, subsequent multiple allergen supplements will be available through 30-day maintenance kits.

Turning back to FIG. 1, it is a table that illustrates an exemplary dosing regimen for a three-allergen early introduction system, which is one particular version of the kit. According to this embodiment, the amount and type of protein is listed alongside the day of the guided program. Day 1 is the exposure dose of cow's milk protein. Day 2 repeats this dose for promotion of tolerance as well as for identification of delayed reactions. The inventor considers two days at the exposure dose to be long enough for the infant's caregiver to observe if there has been any delayed reaction, yet not unnecessarily prolonging the time to reach the maintenance dose. Day 3 increases this dose as part of the graded introduction method. Day 4 repeats Day 3's dose for promotion of tolerance as well as for identification of delayed reactions. The exposure dose of the cow's milk powder protein will preferably be given for two days and will range between about 0.05 and 0.5 grams and will preferably be about 0.2 grams, with the exposure dose being increased after two days to the maintenance dose, which will range between about 0.2 and 1 grams and will preferably be about 0.57 grams. Day 5 includes the previous maintenance dose of cow's milk protein, with the addition of an exposure dose of cooked egg white protein. Day 6 includes the previous maintenance dose of cow's milk protein, and repeats Day 5's dose of cooked egg white protein for promotion of tolerance as well as for identification of delayed reactions. Days 7 and 8 include the previous maintenance dose of cow's milk protein with the addition of a maintenance dose of cooked egg white protein. The exposure dose of the cooked egg white powder protein will preferably be given for two days and will range between about 0.01 and 0.1 grams and will preferably be about 0.025 grams, with the exposure dose being increased after two days to the maintenance dose, which will range between about 0.05 and 0.5 grams and will preferably be about 0.125 grams. Days 9 and 10 include the previous maintenance doses of cow's milk protein and cooked egg white protein, with the addition of an exposure dose of peanut protein which will range between about 0.05 and 0.3 grams and will preferably be about 0.1 grams. For days 11 and 12, the packets will include the previous maintenance doses of cow's milk protein and cooked egg white protein, with the addition of a maintenance dose of peanut protein which will range between about 0.1 and 0.9 grams and will preferably be about 0.43 grams. Days 13-30 will follow the same pattern of graded and sequential introduction, until maintenance dosing of milk, egg, and peanut is achieved, and represents the maintenance phase of the system.

Although the chart in FIG. 1 shows first the introduction of cow's milk protein, then cooked egg white protein, and lastly peanut protein, the relative order of the introduction of the cow's milk protein, cooked egg white protein, and peanut protein may not be important and can thus be swapped around; such as first cooked egg white protein, second peanut protein cow's, and third cow's milk protein, or first cooked egg white protein, second peanut cow's, and third milk protein, or first peanut protein, second cow's milk protein, and last cooked egg white protein, etc.

The staged dosing for the various packages described with reference to FIG. 1 are for cow's milk powder, chicken egg powder, and peanut powder. In another embodiment of the invention, the kit and method comprises these three basic protein powders plus one or more additional powders containing different food allergens which can be introduced either after the initial cow's milk powder, chicken egg powder, and peanut powder, or even before and/or interspersed with dosing with the cow's milk powder, the chicken egg powder, and the peanut powder. However, since cow's milk, chicken egg, and peanut allergies as a group constitute about 80% of the common food allergies of childhood, it makes sense to introduce these allergens first. Alternately, in a further embodiment of the invention, the kit and method comprises the administration of the additional powders which will be introduced after the infant has first consumed the starter kit with cow's milk powder, the chicken egg powder, and the peanut powder.

Turning now to the additional powders, they can include tree nuts powder. Some common tree nuts that cause allergies include almonds, Brazil nuts, cashews, chestnuts, filberts/hazelnuts, macadamia nuts, pecans, pistachios, pine nuts, shea nuts and walnuts. Since some people are allergic to some but not all tree nuts, in practice the additional powder will include a blend of different powdered tree nuts. These additional powders can also include whitefish powder. Whitefish is a fisheries term for several species of demersal fish with fins, particularly Atlantic cod (*Gadus morhua*), Caspian kutum (*Rutilus kutum*), whiting (*Merluccius bilinearis*), and haddock (*Melanogrammus aeglefinus*), but also hake (*Urophycis*), pollock (*Pollachius*), or others. The whitefish powder is made from at least one of these dehydrated fish species. These additional powders can likewise include shellfish powder. Shellfish includes shelled mollusks such as abalone, clams, mussels, oysters, scallops and cockles, and crustaceans, such as crabs, shrimps, prawns, lobsters, and crawfish. Most allergies from shellfish are to crustaceans. The shellfish powder can constitute shellfish which is dehydrated and ground to a fine powder. Lastly, the additional powder can comprise wheat powder, soy protein powder, and/or sesame powder. The doses selected for these additional protein powders will be determined based on data regarding provoking doses of each protein and the higher maintenance dose for each protein. These additional proteins will be introduced in the same staged manner with a first lower provoking dose for one and preferably two to three days, followed by the higher maintenance dose that will continue.

FIG. 2 is a chart showing a dosing schedule for an exemplary embodiment of a five allergen early introduction system kit, with the allergens being in cow's milk powder, chicken egg white powder, peanut powder, wheat powder, and soy powder. As noted above, the relative order of administration of the cow's milk powder, chicken egg white powder, peanut powder, wheat powder, and soy powder can be shifted. In this exemplary embodiment, the dosing of the cow's milk powder, chicken egg powder, peanut powder can remain the same as in the three allergen early introduction system kit as in FIG. 1. The dosing of the wheat powder and soy powder will be as follows. The exposure dose of the wheat powder protein will preferably be given for two days (beginning on day 13) and will range between about 0.05 and 0.5 grams and will preferably be about 0.1 grams, with the exposure dose being increased after two days to the maintenance dose (beginning on day 15), which will range between about 0.2 and 1 grams and will preferably be about 0.4 grams. Packets of the product will continue to include the maintenance dose of the wheat powder. Next, the exposure dose of the soy powder protein will preferably be given for two days (beginning on day 17) and will range between about 0.05 and 0.5 grams and will preferably be about 0.1 grams, with the exposure dose being increased after two days (beginning on day 19) to the maintenance dose, which will range between about 0.2 and 1 grams and will preferably be about 0.4 grams. Once the maintenance dose is reached (day 19), all subsequent packets of the product will continue to include the maintenance doses of all the allergen containing powders.

FIG. 2 describes a kit with powders containing five allergens, viz., cow's milk, chicken egg white, peanut, wheat, and soy. Other kits are contemplated consisting of other noted food allergens. However, regardless of the kit, each allergen will be introduced in a first introductory, lower dose, which after at least one day, and preferably two days, will be increased to a higher maintenance dose. It is also possible that an intermediate dose be given, or that the maintenance dose can be increased gradually in additional steps.

Turning to FIG. 3, there is shown three stick packs for Day 1, Day 2, and Day 3 of an exemplary kit of the invention, which would preferably contain 30 such packs, each sequentially numbered, and containing the amount of allergen containing powder as noted in FIG. 1. Accordingly, the various stick packs will contain the various powders containing the allergen(s) in pre-dosed sticks packs, each bearing its unique number so that the infant's caregiver will know which package to mix in with breastmilk, formula, or baby food on which day.

In another preferred embodiment of the invention, the multiple allergen early introduction system comprising daily dietary supplements for use in a stepwise program of daily use, administered to infants. However, unlike the earlier described embodiment, the dietary supplements are pre-incorporated in the appropriate doses in infant formula, in solid foods (e.g., baby food in jars, pouches, cookies and snack bars and the like, and other food items), or in pre-dosed gel packs so that the caregiver does not need to mix separate supplements into the food. As in the earlier described embodiment, the daily program incorporates increases in protein exposure, sequential introduction, and promotion of tolerance. First exposure formulations use protein amounts determined to be in a range of low provoking doses, as established in the medical literature. By utilizing low provoking doses, reactions if they do occur are significantly more likely to be mild in nature. In the event of any reaction, including but not limited to rashes or gastrointestinal upset, parents and other caregivers are able to present an exact description of exposure history to their pediatrician or allergist. After it has been confirmed that the exposure dose of a particular protein is well tolerated, the infant will continue to be administered the infant formula, solid foods, or the pre-dosed gel packs packets containing the protein(s), which subsequent infant formula, solid foods, or the pre-dosed gel packs packets containing the protein(s) will include a higher, "maintenance" dose of the now cleared protein. Thus, each day's food with the supplement involves either 1) duplication of previous allergen amounts to promote tolerance and allow for detection of delayed reactions, 2) increase of previous allergen amount to achieve maintenance dosing levels, or 3) addition of a new food allergen for sequential introduction. Once the food with an allergen has been introduced, it is included in all subsequent days of the guided program.

The "exposure" phase involves graded increases in allergen amount as well as sequential introduction of new allergens. Once maintenance levels of each have been attained, continuation at these levels is done through daily administration during the "maintenance" phase of the food.

An exemplary introduction kit contains a 30-day supply consisting of daily food items containing the supplements for both the exposure and maintenance phase. Continuation kits contain the maintenance phase food with formulations only can also be provided.

The formulations and duration of the exposure phase depends on the number and type of allergens introduced. The dosing of the various allergens can follow the same exemplary dosing chart as provided in FIG. 1 for a three-allergen introduction system. Again, FIG. 1 is illustrative, and the guided system is not limited to a three-allergen system and the method described above applies to additional allergens as well.

As discussed, the invention has many different features, variations and multiple different embodiments. The invention has been described in this application at times in terms of specific embodiments for illustrative purposes and without the intent to limit or suggest that the invention conceived is only one particular embodiment. It is to be understood that the invention is not limited to any single specific embodiments or enumerated variations. Many modifications, variations and other embodiments of the invention will come to mind of those skilled in the art to which this invention pertains, and which are intended to be and are covered by both this disclosure. It is indeed intended that the scope of the invention should be determined by proper interpretation and construction of the disclosure, including equivalents, as understood by those of skill in the art relying upon the complete disclosure at the time of filing.

The disclosed method and kit is unique when compared with other known methods and kits solutions because it provides an opportunity for early introduction of multiple allergens to infants even prior to when they may be developmentally ready for solid food, via easy suspension in breast milk or infant formula, or provided already mixed in with food. The use of multiple allergens addresses the majority of food allergy causes rather than just one allergen. As noted above, the preferred embodiment with the three common allergens in cow's milk, hen's egg whites, and peanuts, this represents the foods responsible for >80% of childhood food allergy. Similarly, the method is unique in that introduction is in a graded dose increase fashion, facilitating prompt and early identification of potential allergic reactions which if they occur, are more likely to be mild. Similarly, the disclosed method is unique when compared with other known processes and solutions in that multiple allergens are introduced in a sequential fashion, so the specific food allergen involved in potential reactions can be identified.

The disclosed kit is unique in that it is structurally different from other known devices or solutions. More specifically, the kit is unique due to the presence of multiple allergens within the maintenance phase of the guided system kit. The daily formulations consist of unique and distinct doses to achieve sequential as well as graded introduction, based on protocols from the early introduction literature. The components of the daily powders are of sufficiently low particle size, in particular less than about 200 microns, to allow for easy passage through infant bottle nipples. Furthermore, the formulations are specifically designed and tested to allow for easy mixing with breast milk or infant formula. Regarding the kit, a variety of verbal and pictorial instructions allow for easy compliance with the sequence of daily administration.

Furthermore, the process and method of using the kit is likewise unique. More specifically, the disclosed process and method owes its uniqueness to the fact that it provides families with detailed information on the precise identity and amount of food allergen exposure, in the event of adverse food reactions, to be provided to relevant healthcare professionals. Based on the day of the program, families know exactly which food allergens have been administered, how much, and when. Any other approach that does not stagger the introduction of individual allergens over a time series would not offer this benefit of tracing adverse reactions to their cause.

The preferred embodiments of this invention have been disclosed, however, so that one of ordinary skill in the art would recognize that certain modifications would come within the scope of this invention.

What is claimed is:

1. A method for the introduction of premeasured doses of at least two allergens to an infant to decrease the infant's risk for developing allergies, the method comprising the steps of:
   (a) administering to the infant a first allergen at an exposure dose for the first allergen for one or more days;
   (b) subsequently administering to the infant the first allergen at a maintenance dose for the first allergen for multiple days;
   (c) subsequently administering to the infant the first allergen at the maintenance dose and a second allergen at an exposure dose for the second allergen for one or more days; and
   (d) subsequently administering both the first and the second allergens at maintenance doses for each allergen for multiple days;
   wherein the exposure dose may optionally be gradually increased, and
   wherein the exposure dose of the first allergen and the exposure dose of the second allergen are lower than the maintenance dose of the first allergen and the maintenance dose of the second allergen, respectively.

2. The method of claim 1 further including the step of:
   continuing the maintenance doses of the first and second allergens until the premeasured doses for each of the allergens are fully consumed.

3. The method of claim 1 wherein the maintenance doses are continued for several months until the infant is regularly consuming foods containing the first and second allergens as part of its diet.

4. The method of claim 1 further including the steps of:
   (a) administering to the infant a third allergen at an exposure dose for the third allergen for one or more days, and
   (b) subsequently administering to the infant the first, the second, and third allergens at maintenance doses for each of the allergens for multiple days, wherein the exposure dose of the third allergen is lower than the maintenance dose of the third allergen.

5. The method of claim 4 further including the step of:
   continuing the maintenance doses of the first, the second and third allergens until the premeasured doses for each of the allergens are consumed.

6. The method of claim 4, further including the steps of:
   (a) administering the first, second, and third allergens at the maintenance doses along with at least a fourth allergen at an exposure dose for the fourth allergen for one or more days,
   (b) subsequently administering the first, second, third, and fourth allergens at a maintenance dose for each of the allergens for multiple days, wherein the exposure dose of the fourth allergen is lower than the maintenance dose of the fourth allergen.

7. The method of claim 4 wherein:
   (a) another allergen is administered at a first exposure dose for one or more days along with the maintenance doses of the previously administered allergens, and
   (b) subsequently administering said other allergen at a maintenance dose along with the maintenance doses of the previously administered allergens for multiple days, and wherein the exposure doses of said other allergen is lower than the maintenance doses of said other allergen; and
   (c) sequentially repeating steps (a) and (b) above for as many additional allergens as desired.

8. The method of claim 6 further including the step of:
   continuing the maintenance doses of the plurality of allergens until the premeasured dose for each of the plurality of allergens is fully consumed.

9. The method of claim 1 wherein the first and second allergens are each selected from the group consisting of cow's milk, egg, peanut, wheat, soy, sesame, fish, shellfish, and tree nuts.

10. The method of claim 6 wherein the plurality of allergens are each selected from the group consisting of cow's milk, egg, peanut, wheat, soy, sesame, fish, shellfish, and tree nuts.

11. The method of claim 1 wherein the premeasured doses of allergens are mixed into the infant's breast milk, formula, or food and administered enterally.

12. The method of claim 11 wherein the allergens consist of particles having a particle size of less than about 200 microns.

13. The method of claim 1 wherein the premeasured doses of allergens are mixed into the infant's breast milk or formula and administered enterally via an infant bottle.

14. The method of claim 13 wherein the allergens comprise particles of sufficiently small size to readily pass through the nipple of a newborn infant bottle.

15. The method of claim 9 wherein the exposure dose of each allergen is between about 0.01 and 0.3 grams and the maintenance dose of each allergen is between about 0.05 and 1 grams.

16. The method of claim 4 wherein the first allergen comprises cow's milk and the exposure dose of the first allergen is about 0.2 grams of the cow's milk protein, wherein the maintenance dose of first allergen is about 0.4 grams of cow's milk protein, wherein the second allergen comprises egg and the exposure dose of the second allergen is about 0.03 grams of the egg protein, wherein the maintenance dose of second allergen is about 0.1 grams of the egg protein, wherein the powder with the third allergen comprises peanut and the exposure dose of the third allergen is about 0.1 grams of the peanut protein, and wherein the maintenance dose of third allergen is about 0.4 grams of the peanut protein.

17. The method of claim 1 wherein the premeasured doses are in a form of a) pre-dosed daily packets, packages, or pouches, b) measured powder supplements, c) gels, d) infant formula or e) other foods.

18. The method of claim 1 wherein the premeasured doses are in the form of sequentially numbered packages so that users are guided when to administer each respective package.

19. A method for the introduction of premeasured doses of at least two allergens to an infant to decrease the infant's risk for developing allergies, the method comprising the steps of:
   (a) administering to the infant a first allergen at an exposure dose of 0.01-0.3 grams for at least one day;
   (b) subsequent to the administration of the exposure dose of the first allergen, administering to the infant the first allergen at a maintenance dose of 0.05-1 grams for at least two days, wherein the exposure dose of the first allergen is lower than the maintenance dose of the first allergen;
   (c) subsequent to the administration of the maintenance dose of the first allergen, administering to the infant the first allergen at a maintenance dose of 0.05-1 grams along with a second allergen at an exposure dose of 0.01-0.3 grams for at least one day; and
   (d) subsequent to the administration of the maintenance dose of the first allergen along with the exposure dose of the second allergen, administering both the first and the second allergens at maintenance doses of 0.05-1 grams for at least two days, wherein the exposure dose of the second allergen is lower than the maintenance dose of the second allergen.

* * * * *